United States Patent
Yokokawa

(10) Patent No.: US 12,378,509 B2
(45) Date of Patent: Aug. 5, 2025

(54) METHOD FOR PRODUCING CELL CLUSTER GROUP AND DEVICE FOR PRODUCING SAME

(71) Applicant: JSR Corporation, Tokyo (JP)

(72) Inventor: Yuki Yokokawa, Tokyo (JP)

(73) Assignee: JSR Corporation, Tokyo (JP)

( * ) Notice: Subject to any disclaimer, the term of this patent is extended or adjusted under 35 U.S.C. 154(b) by 876 days.

(21) Appl. No.: 17/643,464

(22) Filed: Dec. 9, 2021

(65) Prior Publication Data

US 2022/0098535 A1 Mar. 31, 2022

Related U.S. Application Data

(63) Continuation of application No. PCT/JP2020/016284, filed on Apr. 13, 2020.

(30) Foreign Application Priority Data

Jun. 20, 2019 (JP) .................. 2019-114888

(51) Int. Cl.
| | |
|---|---|
| C12M 3/00 | (2006.01) |
| C12M 1/00 | (2006.01) |
| C12M 1/26 | (2006.01) |
| C12N 5/071 | (2010.01) |

(52) U.S. Cl.
CPC ............ *C12M 21/08* (2013.01); *C12M 23/20* (2013.01); *C12M 33/04* (2013.01); *C12M 45/05* (2013.01); *C12N 5/068* (2013.01); *C12N 2533/90* (2013.01)

(58) Field of Classification Search
None
See application file for complete search history.

(56) References Cited

U.S. PATENT DOCUMENTS

| | | | |
|---|---|---|---|
| 2010/0143913 A1 | 6/2010 | Strehl et al. | |
| 2018/0305669 A1* | 10/2018 | Hancock | C12N 5/067 |
| 2019/0002834 A1* | 1/2019 | Tanabe | C12N 5/0696 |

FOREIGN PATENT DOCUMENTS

| | | |
|---|---|---|
| JP | 2019-502382 A | 1/2019 |
| WO | WO 2017/115865 A1 | 7/2017 |
| WO | WO 2017/117333 A1 | 7/2017 |
| WO | WO 2018/011558 A1 | 1/2018 |

OTHER PUBLICATIONS

International Search Report issued Jun. 23, 2020 in PCT/JP2020/016284 filed on Apr. 13, 2020, 5 pages (with English Translation).
Ivascu et al., "Rapid Generation of Single-Tumor Spheroids for High-Throughput Cell Function and Toxicity Analysis", Journal of Biomolecular Screening 11(8), 2006, pp. 922-932.
Ayano, "New human iPS cell clump mass culture technology using multi-dimple", Seibutsu-kogaku kaishi, vol. 96, No. 7, 2018, pp. 384-386.

* cited by examiner

*Primary Examiner* — Nghi V Nguyen
(74) *Attorney, Agent, or Firm* — Oblon, McClelland, Maier & Neustadt, L.L.P.

(57) ABSTRACT

This method for producing a cell cluster group comprises: a step for putting, into a well, a cell suspension obtained by suspending dispersed cells in a medium, using a cell incubator which includes the well and two or more recesses formed in the bottom of the well and in which the area of an opening of each recess in plan view is at most 1 $mm^2$; a step for centrifuging the cell incubator; and a step for culturing the dispersed cells in the recesses.

10 Claims, 3 Drawing Sheets

METHOD FOR PRODUCING CELL CLUSTER GROUP AND DEVICE FOR PRODUCING SAME

CROSS-REFERENCE TO RELATED APPLICATION

This application is a continuation application based on PCT Patent Application No. PCT/JP2020/016284, filed on Apr. 13, 2020, which claims the benefit of priority of the prior Japanese Patent Application No. 2019-114888 filed on Jun. 20, 2019, the content of which is incorporated herein by reference.

TECHNICAL FIELD

The present invention relates to a method for producing a cell cluster group and a production device of the cell cluster group.

BACKGROUND

In the testing of new drugs, in vitro studies using cultured cells have been conducted before in vivo studies in which new drugs are administered to animals or humans. However, results obtained from in vitro studies are often different from those obtained from in vivo studies.

Organoids are cell clusters having structures and functions similar to organs in vivo. Therefore, the results of in vitro studies using organoids are considered to be similar to those obtained from in vivo studies. Namely, it is considered that in vitro studies using organoids can facilitate research to understand the causes of disease and develop therapeutics (see WO 2018/011558).

SUMMARY

Problems to be Solved by the Invention

The present invention aims to provide a production method of a uniformly sized cell cluster group and a production device of the cell cluster group.

Means to Solve the Problems

The present invention encompasses the following aspects.
(1) A production method of a cell cluster group, including: a step in which a cell suspension in which dispersed cells are suspended in a culture medium is put into a well of a cell-cultivation container including the well and at least two recesses formed in a bottom face of the well, an area of an opening of each recess in plan view being 1 $mm^2$ or less; a step in which the cell-cultivation container is centrifuged to move the dispersed cells in the recesses; and a step in which the dispersed cells are cultured in the recesses.
(2) The production method of a cell cluster group according to (1), wherein a depth of each recess is 100 μm to 1000 μm.
(3) The production method of a cell cluster group according to (1) or (2), wherein each recess has a cylindrical shape or a conical shape.
(4) The production method of a cell cluster group according to any one of (1) to (3), wherein a tessellation ratio of openings of the recesses in the bottom face of the well is 5% to 99.9%.
(5) The production method of a cell cluster group according to any one of (1) to (4), wherein the number of the recesses in the well is 2 to 500.
(6) The production method of a cell cluster group according to any one of (1) to (5), wherein the number of the dispersed cells in the cell suspension is 10 cells/μL to 5,000 cells/μL.
(7) The production method of a cell cluster group according to any one of (1) to (6), wherein extracellular matrix is mixed in the culture medium.
(8) The production method of a cell cluster group according to any one of (1) to (7), wherein an inner wall surface of each recess has cell-non-adhesiveness.
(9) The production method of a cell cluster group according to any one of (1) to (8), wherein an inner wall surface of each recess has a fine protrusion structure.
(10) The production method of a cell cluster group according to any one of (1) to (9), wherein an inner wall surface of each recess is coated with a cell-non-adhesiveness-imparting agent.
(11) The production method of a cell cluster group according to any one of (1) to (10), wherein the dispersed cells contain dispersed gastrointestinal stem cells.
(12) The production method of a cell cluster group according to any one of (1) to (11), wherein the cell-cultivation container is centrifuged at a centrifugal force of 200×g to 1000×g.
(13) A production device of a cell cluster group, including: a support member configured to support a cell-cultivation container including a well and at least two recesses formed in a bottom face of the well, an area of an opening of each recess in plan view being 1 $mm^2$ or less; a cell suspension container configured to store a cell suspension in which dispersed cells are suspended in a culture medium; a pipette configured to draw the cell suspension thereinto and eject the cell suspension into the well of the cell-cultivation container; a pipette-moving mechanism configured to move the pipette in a vertical and horizontal direction; a centrifuging member configured to centrifuge the cell-cultivation container; a cultivation room configured to house the cell-cultivation container to culture the dispersed cells; and a controller configured to control the pipette-moving mechanism.

The present invention also encompasses the following aspects.
(P1) A production method of an organoid, including: a step in which a tissue or an organoid is dispersed into single cells, suspended in a culture medium, and then seeded in a cell culture plate; and a step in which the cells are incubated to allow proliferation of the cells to form the organoid, wherein the cell culture plate includes one or plural wells, and the wells have plural recesses in the bottom face thereof.
(P2) The production method of an organoid according to (P1), wherein the surface of the recesses has cell-non-adhesiveness.
(P3) The production method of an organoid according to (P1) or (P2), wherein the surface of the recesses has an uneven pattern.
(P4) The production method of an organoid according to any one of (P1) to (P3), wherein the surface of the recesses is coated with a polymer.

(P5) The production method of an organoid according to (P4), wherein the polymer is a copolymer including a hydrophilic repeating unit (A) and an adsorptive repeating unit (B).

(P6) The production method of an organoid according to (P5), wherein the adsorptive repeating unit (B) is derived from at least one selected from the group consisting of (meth)acrylates and (meth)acrylamides.

(P7) The production method of an organoid according to any one of (P1) to (P6), wherein the culture medium contains extracellular matrix.

(P8) The production method of an organoid according to (P7), wherein the extracellular matrix is dissolved or dispersed in the culture medium.

(P9) The production method of an organoid according to any one of (P1) to (P8), wherein the culture medium is serum-free culture medium.

(P10) The production method of an organoid according to any one of (P1) to (P9), wherein the organoid is a gastrointestinal organoid.

(P11) The production method of an organoid according to any one of (P1) to (P10), wherein the organoid is derived from mouse or human.

(P12) The production method of an organoid according to any one of (P1) to (P11), further including an aggregation step in which the cells are aggregated in the recesses.

(P13) The production method of an organoid according to (12), wherein the aggregation step is conducted by centrifugation.

(P14) The production method of an organoid according to (13), wherein the centrifugation is conducted at a centrifugal force of 200×g to 1000×g for 1 minute to 30 minutes.

(P15) A production device of an organoid, including: a support member configured to support a cell culture plate; a cell suspension container configured to store a culture medium in which cells obtained by dispersing a tissue or an organoid into single cells are suspended; a seeding member configured to seed the cells on the cell culture plate; and a cultivation room configured to house the cell culture plate on which the cells are seeded to maintain the cells under an atmosphere in which proliferation of the cells is allowed; wherein the cell culture plate includes one or plural wells, and the wells have plural recesses in the bottom face thereof.

(P16) The production device of an organoid according to (P15), wherein the surface of the recesses has cell-non-adhesiveness.

(P17) The production device of an organoid according to (P15) or (P16), wherein the surface of the recesses has an uneven pattern.

(P18) The production device of an organoid according to any one of (P15) to (P17), wherein the surface of the recesses is coated with a polymer.

EMBODIMENTS FOR CARRYING OUT THE INVENTION

Figure 1:
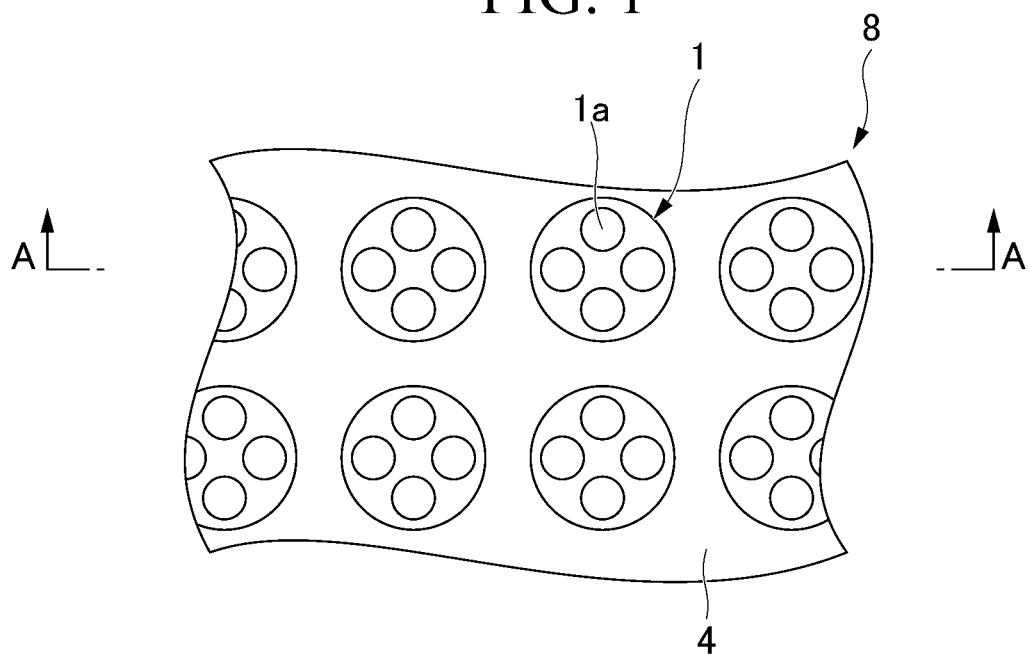
FIG. 1 is a plan view of a cell-cultivation container 8.

Although the present invention will be described in more detail below with reference to embodiments, the present invention is not limited to the following embodiments.

Components exemplified herein, such as components in a culture medium or components used in each step, may be used alone, or may be used in combination of at least two thereof, unless otherwise is stated.

The term indicating a numerical range such as "A to B" means "A or more and B or less".

In the present specification, aggregates of cells are referred to as cell clusters. Among the cell clusters, cell clusters that have structures similar to those of organs in vivo and partially reproduced functions of organs in vivo are referred to as organoids.

In the present specification, the term "cell cluster group" refers to a group of cell clusters containing at least two cell clusters.

Production Method of Cell Cluster Group

A production method of a cell cluster group according to the present embodiment includes: a step in which a cell suspension in which dispersed cells are suspended in a culture medium is put into a well of a cell-cultivation container including the well and at least two recesses formed in the bottom face of the well, an area of an opening of each recess in plan view being 1 mm$^2$ or less (hereinafter, may be referred to as "step (a)"); a step in which the cell-cultivation container is centrifuged to move the dispersed cells in the recesses (hereinafter, may be referred to as "step (b)"); and a step in which the dispersed cells are cultured in the recesses (hereinafter, may be referred to as "step (c)").

In the present embodiment, the dispersed cells can be moved into the recesses together with the culture medium by centrifuging the suspension in which the dispersed cells are suspended in the culture medium. Since the uniform centrifugal force is applied to the dispersed cells in the cell-cultivation container by centrifugation, almost the same number of dispersed cells can be moved to each recess. In addition, formation of a significantly large cell cluster is prevented by culturing the dispersed cells in the recesses. Thus, a uniformly-sized cell cluster group can be obtained.

It is assumed that keeping the dispersed cells in narrow spaces, such as recesses, makes the distance between the cells shorter, thereby improving the efficiency of the signal transduction between the cells and thus improving the culturing efficiency of the cells.

In addition, it is assumed that keeping the dispersed cells in narrow spaces, such as recesses, makes the distance between the cells in the recesses uniform, thereby obtaining a uniformly-sized cell cluster group.

<Step (a)>

In the step (a), a suspension in which dispersed cells are suspended in a culture medium is put into (a) well(s) of a cell-cultivation container including the well(s) and at least two recesses formed in the bottom face of the well. The area of an opening of each recess in plan view is 1 mm$^2$ or less.

<<Dispersed Cells>>

Examples of the dispersed cells include cells obtained by subjecting cell tissue fragments to dispersion treatment, and cells obtained by subjecting cell clusters such as organoids obtained by proliferation or differentiation of the cells to dispersion treatment. Examples of the cell tissue fragments include tissue fragments of adipocytes, chondrocytes, osteocyte, muscle cells, vascular cells, immune cells, endothelial cells, neurons, hepatocytes, pancreatic cells, small intestinal cells, and large intestinal cells.

In the dispersed cells, stem cells that can proliferate or differentiate are contained. In the dispersed cells, cells other than stem cells may be contained. Examples of the stem cells include: pluripotent stem cells such as ES cells and iPS cells, and somatic stem cells constituting tissues in a living organism. As the stem cells, stem cells maintained by culture or primary stem cells obtained from a tissue removed from a living organism may be used.

In the dispersion treatment, cells are dispersed by enzyme treatment or physical treatment to separate cell groups consisting of 100 cells or less, preferably 50 cells or less, and more preferably 5 cells or less. The dispersion treatment may be conducted by treating cell groups with a cell dispersion liquid.

Examples of the cell dispersion liquid include proteolytic enzymes such as trypsin, dispase, and collagenase, and xylate agents such as EDTA.

The cells may be diluted with a dilution liquid after dispersion treatment, so as to prevent cell death caused by the cell dispersion liquid. Examples of the dilution liquid include basic culture medium mentioned below. The dilution liquid may contain a supplement, an antibacterial agent, and a buffer.

<<Culture Medium>>

Any types of culture medium may be used, provided that the culture medium allows formation of cell clusters. The culture medium generally has a pH of 5 to 12. The culture medium may be prepared by adding a substance which controls a signal transduction pathway such as an agonist or antagonist, a supplement, an antibacterial agent, a buffer, and the like to the basic culture medium, and then mixing them. In the culture medium, extracellular matrix (ECM) is preferably mixed. The dispersed cells can be put into recesses favorably by mixing ECM with the culture medium.

Examples of the basic culture medium include DMEM/F12 medium, RPMI 1640 medium, BME medium, BGJb medium, CMRL 1066 medium, Glasgow MEM (GMEM) medium, Improved MEM Zinc Option medium, IMDM medium, Medium 199, Eagle MEM medium, aMEM medium, DMEM medium, F-12 medium, IMDM/F12 medium, Ham's medium, and Fischer's medium; and mixtures thereof.

Examples of the agonist include: enhancers in the Wnt signal transduction pathway such as Wnt3a, Wnt4a, and R-spondin; and enhancers in the IGF signal transduction pathway such as IGF-1 and IGF-2.

Examples of the antagonist include: GSK-3f3 inhibitors such as CHIR9901 and Kenpaullone; TGF-β signal transduction pathway inhibitors such as A83-01 and SB-431542; Rho kinase signal transduction pathway inhibitors such as Y-27632 and H-1152; and BMP signal transduction pathway inhibitors such as Noggin and dorsomorphin.

Examples of the supplement include: a neuron culture supplement such as "B-27 serum-free supplement" (product name, manufactured by Thermo Fisher Scientific Inc.); a glutamine-containing supplement such as "GlutaMax" (product name, manufactured by Thermo Fisher Scientific Inc.) including L-glutamine, L-alanyl-L-glutamine, and the like; an amino acid aqueous solution such as "MEM Non-Essential Amino Acid Solution" (product name, manufactured by Thermo Fisher Scientific Inc.) and 2-mercaptoethanol.

Examples of the antibacterial agent include penicillin-based antibiotics, cephem-based antibiotics, macrolide-based antibiotics, tetracycline-based antibiotics, fosfomycin-based antibiotics, aminoglycoside-based antibiotics, and new quinolone-based antibiotics.

Examples of the buffer include HEPES buffer and PBS buffer.

It is preferable that extracellular matrix (ECM) be mixed in the culture medium. Examples of the ECM include: components contained in the basement membrane; and glycoproteins present in gaps between cells. Examples of the components contained in the basement membrane include IV-type collagen, laminin, heparan sulfate proteoglycan, and entactin. Examples of the glycoproteins present in gaps between cells include collagen, laminin, entactin, fibronectin, and heparin sulfate. As the ECM, a commercially-available product containing ECM may be used. Examples of the commercially-available product containing ECM include: Matrigel (trademark, manufactured by Corning Incorporated), and human-type laminin (manufactured by Sigma-Aldrich Co., LLC.).

In the culture medium, 0.8% to 10% (v/v) of ECM may be contained. ECM may be dispersed or dissolved in the culture medium.

<<Cell-Cultivation Container>>

Figure 2:
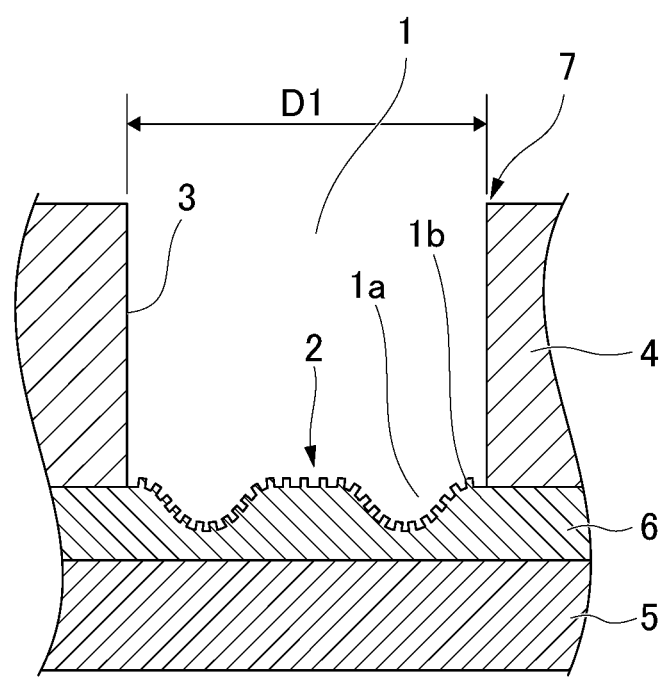
FIG. 2 is a partial cross-sectional view of a cell-cultivation container 8.

One aspect of the cell-cultivation container according to the present embodiment is illustrated in FIG. 1 and FIG. 2. A cell-cultivation container 8 includes one or plural wells 1, and the well 1 has at least two recesses 1a in the bottom face 2 thereof. It is preferable that the surface of the recess 1a of the cell-cultivation container have cell-non-adhesiveness. As shown in FIG. 2, the recess 1a may have fine protrusions 1b.

The cell-cultivation container 8 mainly includes: a cell culture plate main body 4 constituting a side wall (inner periphery) 3 of the well 1; a bottom plate 5 constituting a bottom wall of the well 1; and a well plate sheet 6 constituting the bottom face 2 of the well 1. The cell culture plate main body 4 is a thick plate in which plural through-holes 7 are formed. The well plate sheet 6 is laminated between the cell culture plate main body 4 and the bottom plate 5. The recesses 1a are formed on the surface of the well plate sheet 6.

The shape of the cell-cultivation container 8 in plan view may be a rectangular shape, a circular shape, or the like. In the case where the shape of the cell-cultivation container 8 in plan view is a rectangular shape, the lengths of the short side and the long side may be appropriately adjusted depending on the size or the arrangement density of the well 1, the size of a device used to conduct cultivation, or the like. For example, there are 96-well, 384-well, and 1536-well microplate standards ANSI/SBS 1-2004 to 4-2004.

The cell culture plate main body 4 and the bottom plate 5 are preferably made of a material which does not adversely affect cultured cells and is not denatured by the culture medium. Examples of such a material include: polypropylenes; polyesters; polyolefins; polystyrenes; polyurethanes; celluloses; regenerated celluloses; polycarbonates; polyamides; polyimides; fluorine-containing resins such as polytetrafluoroethylene; acrylic resins; polylactic acids; polyglycolic acids; styrene-based copolymer resins; acrylic styrene-based resins; polycarbonate-based resins; polyvinyl alcohol-based resins; ethylene-vinyl alcohol-based copolymer resins; thermoplastic elastomers; vinyl chloride-based resins; and silicone resins; and glass-containing materials.

Examples of the shape of the well 1 include a prismatic shape, a prismoidal shape, a cylindrical shape, a conical shape, a cylindroid shape, and an elliptic-conical shape, each axis of which is perpendicular to the bottom face 2 of the cell-cultivation container 8. The bottom face 2 of the cell-cultivation container 8 refers to the "bottom face of the well 1 formed by contacting the cell culture plate main body 4 with the well plate sheet 6 in the cell-cultivation container 8". Among these, the shape of the well 1 is preferably a cylindrical shape or a conical shape, more preferably a conical shape, and even more preferably a conical shape in which an opening is larger than the bottom face. Namely, it is more preferable that the inner diameter of the well 1 be gradually increased from the bottom surface 2 toward the opening. In the case where the shape of the well 1 is such a shape, the opening is relatively large, and therefore the introduction of the culture medium into the well 1 can be readily carried out.

The lower limit of the diameter D1 of the bottom face of the well 1 is preferably 0.5 mm, more preferably 0.8 mm, and even more preferably 1 mm. The upper limit of the diameter D1 of the bottom face is preferably 10 cm, more preferably 5 cm, and even more preferably 3.5 cm. In the case where the diameter D1 is the lower limit or more, the introduction of the culture medium into the well 1 can be readily carried out. In the case where the diameter D1 of the bottom face is the upper limit or less, the space that does not contribute to cell culture is reduced, and the culturing efficiency can be improved when three-dimensional culture is performed using the cell culture plate. In the case where the shape of the well 1 is a cylindroid shape or an elliptic-conical shape, the diameter D1 of the bottom face of the well 1 refers to the average value of the major axis and the minor axis. In the case where the cross-section of the well 1 is a rectangle, the diameter D1 of the bottom face of the well 1 refers to the average value of the long side and the short side.

In the case where the shape of the well 1 is a cylindroid shape or an elliptic-conical shape, it is preferable that the flattening ratio of the bottom face thereof be 0.2 or less, and more preferably 0.15 or less. The "flattening ratio" refers to a value obtained by the following formula: (a-b)/a, wherein a is a half-length of the major axis of an ellipse and b is a half-length of the minor axis thereof.

In the case where the well 1 has a prismatic shape, the length ratio of the long side to the short side is preferably 1 to 1.3, and more preferably 1 to 1.2.

The depth of the well 1 is preferably 0.5 mm to 2 cm, more preferably 1 mm to 1.5 cm, and even more preferably 1.2 mm to 1.5 cm. In the case where the depth is within the above-mentioned range, the culture medium can be held stably in the well 1.

The capacity of the well 1 is preferably 0.1 μL to 10 mL, more preferably 0.5 μL to 7 mL, and even more preferably 0.8 μL to 4 mL. In the case where the capacity is within the above-mentioned range, the introduction of the culture medium into the well 1 can be readily carried out.

In the case where there are plural wells 1, the shape thereof is preferably identical to each other.

The bottom face 2 of each well has at least two recesses 1*a*. The dispersed cells are put in each recess 1*a*, thereby obtaining a single cell cluster per recess 1*a*, as a result of which a uniformly-sized cell cluster group can be obtained.

The number of the recesses 1*a* in the bottom face 2 of each well 1 is preferably 2 to 500, more preferably 10 to 300, and even more preferably 50 to 200. In the case where the number of the recesses 1*a* in the bottom face 2 is the lower limit or more, the number of the cell cluster groups to be cultured can be increased. In the case where the number of the recesses 1*a* in the bottom face 2 is the upper limit or less, the recesses 1*a* can be readily formed.

The shape of the recess 1*a* is preferably a solid shape having an axis which is perpendicular to the bottom face 2 of the cell-cultivation container 8 from the viewpoint of the cell-culturing efficiency. Examples of the solid shape include a prismatic shape, a prismoidal shape, a cylindrical shape, a conical shape, a cylindroid shape, and an elliptic-conical shape. Among these, a conical shape or a cylindrical shape is preferable.

Examples of the shape of the opening of the recess 1*a* in plan view include a circular shape, an elliptical shape, and polygons such as a rectangular shape. Among these, a circular shape is preferable. In the case where the shape of the opening of the recess 1*a* in plan view is a circular shape, the shape of the cell cluster can be made closer to a spherical shape.

The area of the opening of the recess 1*a* in plan view is generally 10 mm$^2$ or less, preferably 0.0001 mm$^2$ to 8 mm$^2$, and more preferably 0.01 mm$^2$ to 4 mm$^2$. The area may be 1 mm$^2$ or less, 0.0001 mm$^2$ to 1 mm$^2$, or 0.01 mm$^2$ to 1 mm$^2$. In the case where the area is within the above-mentioned range, a uniformly-sized cell cluster group can be obtained.

In the case where the shape of the recess 1*a* in plan view is a circular shape, the diameter thereof is generally 30 μm to 3000 μm, preferably 100 μm to 2000 μm, and more preferably 150 on to 1000 μm. In the case where the shape of the recess 1*a* in plan view is a polygon, the length of one side thereof is generally 100 μm to 1000 μm, and more preferably 300 μm to 600 μm.

The depth of the recess 1*a* is generally 20 μm to 2000 μm, and preferably 50 μm to 1000 μm, more preferably 100 on to 1000 μm, and most preferably 300 μm to 600 μm.

In the case where the depth of the recess 1*a* is within the above-mentioned range, the size-uniformity of the cell cluster group can be improved.

The tessellation ratio of the openings of the recesses 1*a* in the bottom face 2 is generally 5% to 99.9%, and preferably 10% to 90%. In the case where the tessellation ratio of the openings of the recesses 1*a* in the bottom face 2 is within the above-mentioned range, the dispersed cells are reliably put in the recesses 1*a* even if the dispersed cells are increased, and therefore the size-uniformity of the cell cluster group can be improved.

It is preferable that the recesses 1*a* be arranged regularly in the bottom face 2 of the well 1. The regular arrangement of the recesses 1*a* allows the dispersed cells to be evenly spaced, thereby improving the size-uniformity of the cell cluster group.

It is preferable that the inner wall surface of the recess 1*a* have cell-non-adhesiveness. Examples of a method of imparting cell-non-adhesiveness to the inner wall surface of the recess 1*a* include: a method in which fine protrusions 1*b* are formed on the surface of the recess 1*a*; a method in which the surface of the recess 1*a* is treated with a cell-non-adhesiveness-imparting agent, and a combination thereof.

There are generally plural fine protrusions 1*b*, and the shape of the fine protrusions 1*b* is preferably regular.

The cell-non-adhesiveness-imparting agent contains a polymer generally containing a hydrophilic structure. Examples of such a polymer include polyvinyl alcohol and copolymers having hydrophilic repeating units (A) and adsorptive repeating units (B). Examples of such copolymers include copolymers described in WO 15/119256, WO 05/108554, and WO 13/022085.

<<Cell Suspension>>

The cell suspension may be obtained by suspending the dispersed cells in the culture medium. The suspending process may be generally conducted by vibrating a microtube containing the culture medium and the dispersed cells. The concentration of the cell suspension is generally 10 cells/μL to 5,000 cells/μL, preferably 15 cells/μL to 3,000 cells/μL, and more preferably 25 cells/μL to 1,000 cells/μL. In the case where the concentration is within the above-mentioned range, a cell cluster group having excellent size-uniformity and excellent culturing efficiency can be obtained.

The cell suspension may be generally put in the well of the cell-cultivation container by pipetting.

<Step (b)>

In the step (b), the cell-cultivation container is centrifuged. The cell suspension containing the culture medium and the dispersed cells may be put in the recesses by the centrifugation. Since the centrifugal force is uniformly applied to the dispersed cells in the cell-cultivation container by the centrifugation, the same number of the dispersed cells can be put in each recess, and the formation of a significantly large cell cluster is prevented, as a result of which the uniformly-sized cell cluster group can be obtained.

The number ratio of the dispersed cells in the recesses to the dispersed cells contained in the cell suspension is generally 50% or more, preferably 75% or more, and more preferably 100%. As a result of the movement of most of the dispersed cells contained in the suspension to the recesses, the culture medium component remains outside the recesses in the well, and the number of dispersed cells therein is sufficiently low to facilitate manipulation conducted in the cultivation process, such as culture medium exchange.

Centrifugation of the cell-cultivation container is carried out such that the centrifugal force is applied in a direction toward the depth of the well, preferably in a direction from the opening of the well to the bottom face of the recess, more preferably in a direction in which the incident angle of the vector of the centrifugal force from the opening of the well to the bottom face of the recess becomes 0° or more and less than 90°. The centrifugal force is typically 100×g to 1,000× g, preferably 150×g to 800×g, more preferably 200×g to 1000×g, most preferably 200×g to 600×g. The centrifugation time is usually 1 minute to 30 minutes.

<Step (c)>

In the step (c), the dispersed cells are cultured. The culture medium component in the well may be stirred during cultivation. In addition, the culture medium may be changed appropriately during cultivation. The cultivation conditions may be controlled depending on the type of cells to be dispersed and cultured or the type of the culture medium.

In the case where, for example, dispersed normal cells derived from mouse small intestine are cultured in a culture medium containing a Wnt signaling enhancer, a TGFβ signaling inhibitor, a Rho kinase inhibitor, and a BMP signaling inhibitor, the culturing period is usually 3 days or more, the temperature of the culture medium during cultivation is typically 30° C. to 50° C., and the carbon dioxide content in the culture medium during cultivation is typically between 1% by volume to 15% by volume.

Production Device

A production device according to the present embodiment is a production device of a cell cluster group, and includes: a support member configured to support a cell-cultivation container having (a) well(s) and at least two recesses formed in the bottom face of each well, an area of an opening of each recess in plan view being 1 mm² or less; a cell suspension container configured to store a cell suspension in which dispersed cells are suspended in a culture medium; a pipette configured to draw the cell suspension thereinto and eject the cell suspension into the well(s) of the cell-cultivation container; a pipette-moving mechanism configured to move the pipette in a vertical and horizontal direction; a centrifuging member configured to centrifuge the cell-cultivation container; a cultivation room configured to house the cell-cultivation container to culture the dispersed cells; and a controller configured to control the pipette-moving mechanism. Hereinafter, the above-mentioned well(s) is(are) referred to as "specific well(s)".

Figure 3:
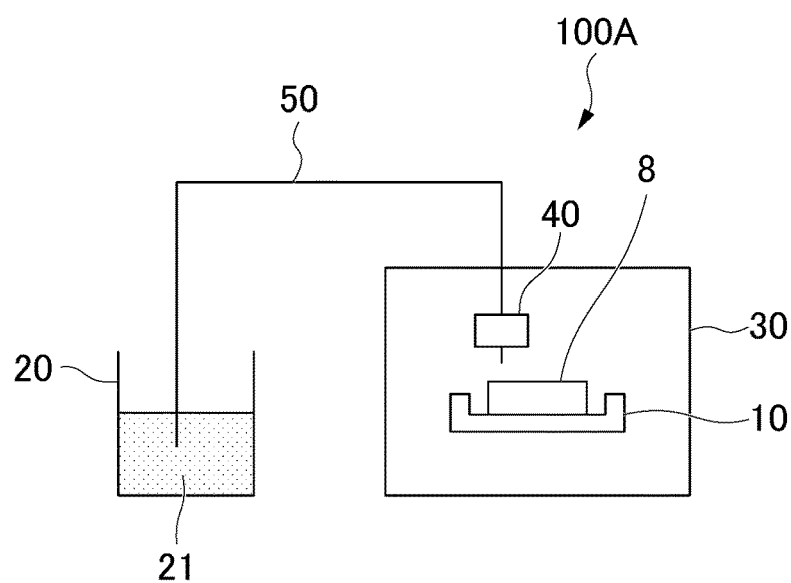
FIG. 3 is a schematic diagram illustrating the construction of a production device 100A of a cell cluster group.

FIG. 3 is a schematic diagram illustrating a production device according to the present embodiment. A production device 100A includes: a support member 10 configured to support a cell-cultivation container 8 having (a) specific well(s) (not illustrated); a cell suspension container 20 configured to store a cell suspension 21 in which dispersed cells are suspended in a culture medium 21; a pipette 40 configured to draw the cell suspension 21 in the cell suspension container 20 and eject the cell suspension into the specific well(s) of the cell-cultivation container 8; a cultivation room 30 configured to house the support member 10. An opening and closing member (not illustrated) is formed in the cultivation room 30 such that the cells are maintained under an atmosphere in which cell-proliferation is allowed and the cell-cultivation container 8 can be inserted or removed.

The cultivation room 30 has a structure that prevents contamination of bacteria and the like in the well(s) of the cell-cultivation container 8. The cultivation room 30 can maintain the atmosphere therein in which a temperature, oxygen concentration, and carbon dioxide concentration are maintained to be suitable to conduct cultivation. A conduit 50 is connected to both the cell suspension container 20 and the pipette 40.

The pipette 40 is equipped with a pump (not illustrated) configured to draw the cell suspension 21 into the pipette 40. The pipette 40 is further equipped with a pipette-moving mechanism (not illustrated) configured to move the pipette 40 in a vertical and horizontal direction along the cell-cultivation container 8 to allow the pipette 40 to eject the cell suspension 21 into the well(s) of the cell-cultivation container 8. The pipette-moving mechanism can be controlled by a controller (not illustrated).

The production device may be used as follows. First, the cell-cultivation container 8 is placed on a support member 10 and the cell suspension 21 is stored in the cell suspension container 20. The cell suspension 21 in the cell suspension container 20 is led through the conduit 50 to be ejected by the pipette 40 into (a) specific well(s) of the cell-cultivation container 8 supported by the support member 10 in the cultivation room 30. In the cell-cultivation container 8 in which the cell suspension 21 is seeded, the cells are cultured to proliferate or differentiate under an atmosphere suitable to conduct cultivation, thereby obtaining cell clusters.

Figure 4:
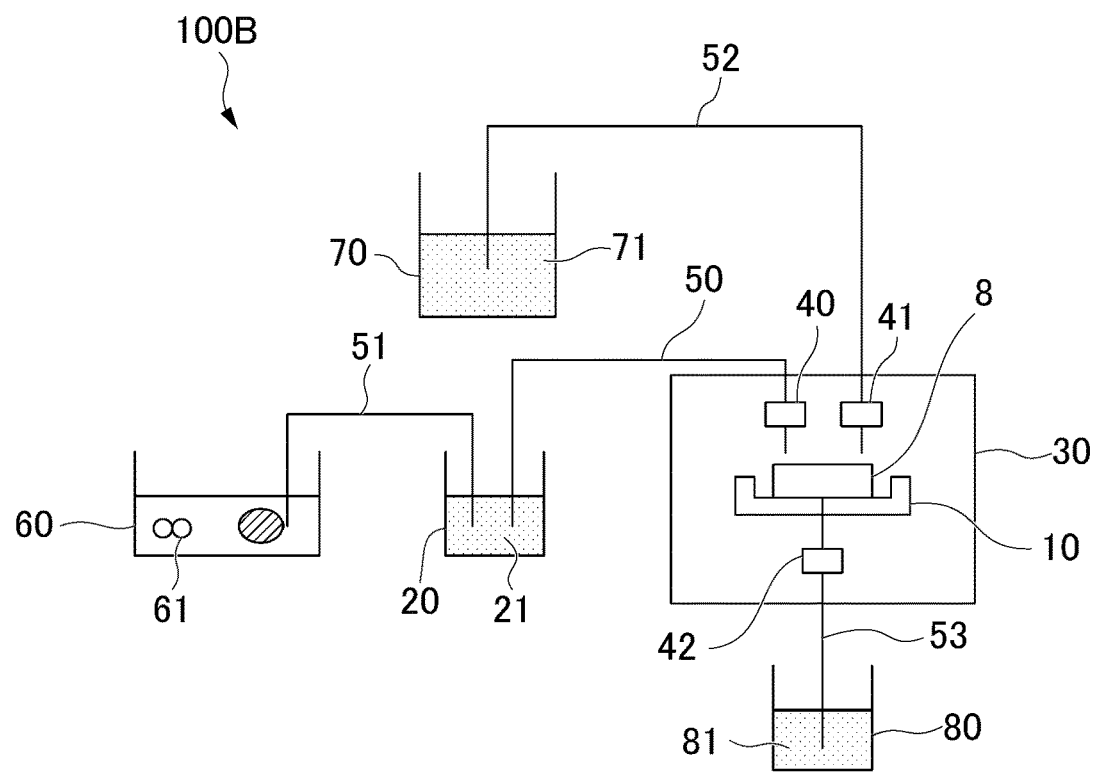
FIG. 4 is a schematic diagram illustrating a production device 100B of a cell cluster group.

FIG. 4 illustrates a variation of the production device according to the present embodiment. The production device 100B further includes: a dispersing container 60 configured to prepare dispersed cells; a culture medium container 70 configured to store the culture medium; and a drainage container 80 configured to store the drained culture medium.

The dispersing container 60 includes: a stirrer 61 configured to stir the culture medium and biological tissue. A tissue removed from the living body, or the like is put in the dispersing container 60, and then stirred by the stirrer 61, thereby dispersing the biological tissue to obtain dispersed cells, and thus the cell suspension 21 in which the dispersed cells are suspended in the culture medium is obtained.

A conduit 51 is connected to both the dispersing container 60 and the cell suspension container 20. The cell suspension 21 in the dispersing container 60 is led through the conduit 51 to be stored in the cell suspension container 20.

The culture medium 71 is stored in the culture medium container 70. The conduit 52 is connected with both the culture medium container 70 and the pipette 41. The culture medium 71 in the culture medium container 70 is led through the conduit 52 to be ejected by the pipette 41 into (a) specific well(s) in the cell-cultivation container 8 housed in the cultivation room 30.

The drained culture medium 71 is stored in the drainage container 80. The conduit 53 is connected with both the drainage container 80 and a suction member 42. The unnecessary culture medium 71 in the specific well(s) of cell-cultivation container 8 is suctioned by the suction member 42, and led through the conduit 53 to be stored in the drainage container 80.

The unnecessary culture medium 71 in the specific well(s) of cell-cultivation container 8 is suctioned by the suction member 42, and led through the conduit 53 to be stored in the drainage container 80 during culturing of the cells. Then, the culture medium 71 in the culture medium container 70 is led through the conduit 52 to be dispensed to the well(s) in the cell-cultivation container 8 by the pipette 41. Thus, the culture medium 71 in the well(s) in the cell-cultivation container 8 is exchanged.

According to the present embodiment, a cell cluster group having excellent size-uniformity can be produced. According to the present embodiment, a cell cluster group, such as an organoid, having uniform quality can be produced further readily, and therefore the organoid can be used further widely in new drug testing.

EXAMPLES

Hereinafter, the present invention will be described in detail with reference to examples, but the present invention is not limited to these examples.

Figure 5:
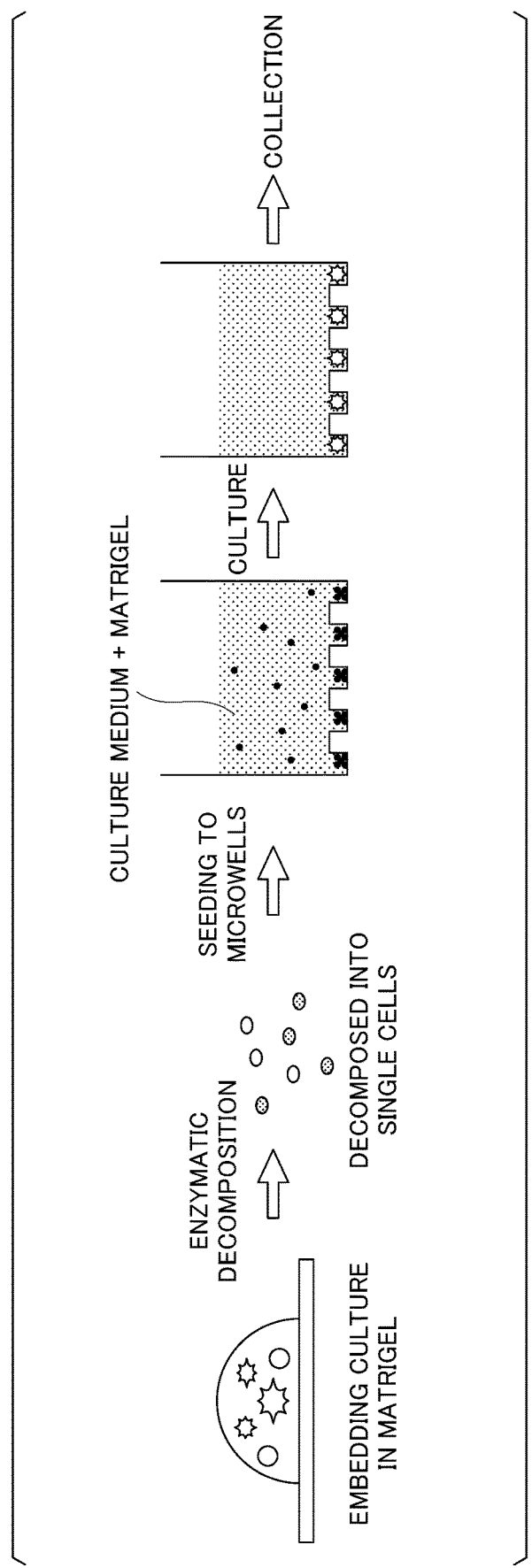
FIG. 5 is a schematic diagram illustrating the procedure of producing a cell cluster group in examples.

FIG. 5 is a schematic diagram showing an overview of the experiment. A dispersing enzyme was contacted with stem cells embedded in Matrigel to be cultured or tissue cell fragments containing stem cells to obtain dispersed cells and then the dispersed cells were suspended in culture medium. The resultant suspension was placed in a cell culture plate and cultured to obtain an organoid. The size-uniformity of the resulting cell clusters was evaluated.

A cell-cultivation container having 96 cylindrical wells and 85 conical recesses (500 μm in diameter and 400 μm in depth) in each well, and a fine protrusion structure on the surface of each recess (hereinafter referred to as "Dimple"); Elplasia (product name, manufactured by KURARAY CO., LTD.) having 96 cylindrical wells and 110 cylindrical recesses (500 μm in diameter and 400 μm in depth) in each well (hereinafter referred to as "Elpalasia"); and SPHERICAL PLATE 5D (product name, manufactured by Mitokogyo Corporation) having 96 pyramidal wells (hereinafter referred to as "Spherical") were used as cell-cultivation containers.

An aqueous solution containing 1% by mass of a polymer having a structural unit of the following formula (1) (hereinafter referred to as "Blockmaster"), LIPIDURE-CM5206 (product name, manufactured by NOF CORPORATION, hereinafter referred to as "LIPIDURE"), and an aqueous solution containing 1% by mass of polyvinyl alcohol (hereinafter referred to as "PVA") were used as cell-non-adhesive-imparting agents.

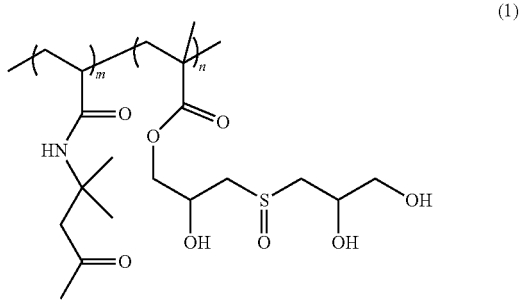

In the formula (1), m:n (mass ratio) is 50:50

The surface of the wells and recesses of the cell-cultivation containers was subjected to surface treatment using the cell-non-adhesiveness-imparting agents by the following procedure.

200 μL of the cell-non-adhesiveness-imparting agent was placed in each well of the cell-cultivation container to make the cell-non-adhesiveness-imparting agent contact with the well and the surface of the recesses, followed by removing the cell-non-adhesiveness-imparting agent. 300 μL of cleaning liquid shown in Table 1 (hereinafter referred to as "cleaning liquid A") was put in each well to wash the well and this washing procedure was repeated three times.

TABLE 1

| Cleaning liquid A |
|---|
| Advanced DMEM/F12 (Thermo Fisher SCIENTIFIC) |
| 100 U/mL Penicillin Streptomycin (Thermo Fisher SCIENTIFIC) |
| 2 mM GlutaMAX-I (Thermo Fisher SCIENTIFIC) |
| 10 mM HEPES (Thermo Fisher SCIENTIFIC) |

Reference Example 1: Expansion Culture of Normal Cells Derived from Mouse Small Intestine Normal cells derived from mouse small intestine (manufactured by STEMCELL Technologies Inc., under the product name of "Mouse Intestinal Organoids") were suspended in an extracellular matrix (manufactured by Corning Incorporated, under the product name of "Corning Matrigel Basement Membrane Matrix" and the product number of 354230) to form a 25 μL dome/well in a flat-bottom 48-well plate (manufactured by Corning Incorporated, under the product name of Costar and the product number of 3548). Then, the 48-well plate was placed in an incubator at 37° C. under a 5% by volume carbon dioxide atmosphere to gel the Matrigel. 300 μL of culture medium having a constitution shown in Table 2 (hereinafter referred to as "culture medium A") was added to each well, and the cells were cultured for 7 days while exchanging the culture medium three times every 2 to 3 days to obtain a mouse small intestinal cell cluster. When the culture medium was exchanged, a culture medium in which Y27632 was not contained in the culture medium A was used. After the cultivation, the culture medium was removed to obtain an expanded culture of normal cells derived from mouse small intestine (hereinafter, referred to as "mouse small intestine normal cell cluster").

TABLE 2

| Culture medium A |
| --- |
| Advanced DMEM/F12 (Thermo Fisher SCIENTIFIC) |
| 100 U/mL Penicillin Streptomycin (Thermo Fisher SCIENTIFIC) |
| 2 mM GlutaMAX-I (Thermo Fisher SCIENTIFIC) |
| 10 mM HEPES (Thermo Fisher SCIENTIFIC) |
| 2 vol % B27 SUPPLEMENT (50×) (Thermo Fisher SCIENTIFIC) |
| 10 nM LEU15-GASTRIN I (SIGMA-ALDRICH) |
| 1 mM N-Acetyl-L-cysteine (SIGMA-ALDRICH) |
| 65 ng/mL mouse EGF (Thermo Fisher SCIENTIFIC) |
| 500 nM A-83-01 (Tocris Bioscience) |
| 10 µM SB202190 (SIGMA-ALDRICH) |
| 1 vol % N2 supplement (Thermo Fisher SCIENTIFIC) |
| 3.5 µM Y27632 (SIGMA-ALDRICH) |
| 5 µg/mL Recombinant Murine Noggin (Peprotech) |
| 5 vol % Rspondin CM |
| 20 vol % Afamin/Wnt3a CM (JSR) |

Example 1: Preparation and Evaluation of Cell Cluster

The mouse small intestine normal cell cluster obtained in Reference Example 1 and an enzyme (TrypLE Express, manufactured by Gibco) were put into microtubes and then dispersed by pipetting. Then, a cleaning liquid containing 100 U/ml of Penicillin Streptomycin (product name, manufactured by Thermo Fisher SCIENTIFIC Inc.), 2 mM GlutamaX-1 (product name, manufactured by Thermo Fisher SCIENTIFIC Inc.) and 10 mM HEPES (product name, manufactured by Thermo Fisher SCIENTIFIC Inc.) in Advanced DMEM/F12 (product name, manufactured by Thermo Fisher SCIENTIFIC Inc.) was put in the microtubes and then centrifuged. The supernatant of the resultant solution in the microtubes was removed after centrifugation, and then the cleaning liquid B was again put into the microtubes and then centrifuged to remove the supernatant of the resultant solution in the microtube, thereby obtaining dispersed cells.

Then, the culture medium A and Matrigel (product name, manufactured by Corning Life Sciences) were mixed to obtain a mixture solution in which the concentration of the Matrigel, relative to the culture medium A, became 5% by volume, and the dispersed cells were suspended in the mixture solution to obtain a cell suspension in which the amount of the dispersed cells became 500 cells/µL.

300 µL of the cleaning liquid A was put in each well of Dimple and then the each well was washed three times. 200 µL of the cell suspension was put in the each well of Dimple and cultured in an incubator at 37° C. under a 5% by volume carbon dioxide atmosphere for 3 days to obtain each cell cluster group. The size of the resultant organoid in each recess was measured by light microscopy and the size-uniformity of the resultant cell cluster group was evaluated on a five-point scale of L1 to L5. On the five-point scale, L1 indicates the lowest size-uniformity of the cell cluster group, and L5 indicates the highest size-uniformity of the cell cluster group. The evaluation results are shown in Table 3.

Examples 2 and 5

Cell cluster groups were prepared in the same way as that of Example 1, except that each cell-cultivation container was previously subjected to surface treatment using a cell-non-adhesiveness-imparting agent shown in Table 3. The size-uniformity of the resultant cell cluster groups was evaluated, and the results thereof are shown in Table 3.

Example 3

A cell suspension was obtained by the same way as that of Example 1. 200 µL of the resultant cell suspension was put into a cell-cultivation container which was previously subjected to surface treatment using a cell-non-adhesiveness-imparting agent shown in Table 3, and then centrifuged using a centrifugal device (manufactured by Beckman Coulter Inc., under the product name of "Allegra X-15R") at a centrifugal force of 400×g for 5 minutes at 25° C. After the centrifugation, cells were cultured in an incubator at 37° C. under a 5% by volume carbon dioxide atmosphere for 3 days to obtain a cell cluster group. The size-uniformity of the resultant cell cluster group was evaluated by the same way as that of Example 1. The evaluation result is shown in Table 3.

Example 4

A cell cluster group was prepared in the same way as that of Example 1, except that a cell-cultivation container shown in Table 3 was used. The size-uniformity of the resultant cell cluster group was evaluated. The evaluation result is shown in Table 3.

Examples 6 to 8

Cell cluster groups were prepared in the same way as that of Example 3, except that each cell-cultivation container which was previously subjected to surface treatment using each cell-non-adhesiveness-imparting agent shown in Table 3 was used. The size-uniformity of the resultant cell cluster groups was evaluated. The evaluation results are shown in Table 3.

Example 9

A cell cluster group was prepared in the same way as that of Example 1, except that Spherical was used as a cell-cultivation container and D-PBS(−) (manufactured by FUJI-FILM Wako Pure Chemical Corporation, hereinafter referred to as PBS) was used as a cleaning liquid A. The size-uniformity of the resultant cell cluster group was evaluated. The evaluation results is shown in Table 3.

TABLE 3

| | Cell-cultivation container | Surface treatment | Centrifugation | Size-uniformity |
| --- | --- | --- | --- | --- |
| Example 1 | Dimple | none | none | L2 |
| Example 2 | Dimple | Blockmaster | none | L3 |
| Example 3 | Dimple | Blockmaster | Yes | L5 |
| Example 4 | Elplasia | none | none | L3 |
| Example 5 | Elplasia | Blockmaster | none | L4 |
| Example 6 | Elplasia | Blockmaster | Yes | L5 |
| Example 7 | Dimple | LIPIDURE | Yes | L5 |
| Example 8 | Dimple | PVA | Yes | L5 |
| Example 9 | Spherical | none | Yes | L3 |

The present invention makes it possible to provide a production method of an organoid having excellent size-uniformity. An organoid having excellent size-uniformity is useful in drug screening in which a large amount of organoid is used to make comparisons.

EXPLANATION OF REFERENCE NUMERALS 1 well
1a recess
1b fine protrusion
2 bottom face
3 inner periphery (side wall)
4 cell culture plate main body
5 bottom plate
6 well plate sheet
7 through-hole
8 cell-cultivation container
10 support member
20 cell suspension container
21 cell suspension
30 cultivation room
40, 41 pipette
42 suction member
50, 51, 52, 53 conduit
60 dispersing container
61 stirrer
70 culture medium container
71 culture medium
80 drainage container
100A production device
100B production device

What is claimed is:

1. A method for production of a cell cluster group, the method comprising:
adding into a well of a cell-cultivation container a cell suspension in which dispersed cells are suspended in a culture medium, wherein the well further comprises at least two recesses formed in a bottom face of the well, and wherein an area of an opening of each of the at least two recesses in plan view is 1 mm$^2$ or less;
centrifuging the cell-cultivation container; and
culturing the dispersed cells in the recesses,
wherein an inner wall surface of each of the at least two recesses is coated with a cell-non-adhesiveness-imparting agent; and
wherein each of the at least two recesses has a cylindrical shape or a conical shape.

2. The method of claim 1, wherein a depth of each of the at least two recesses is from 100 μm to 1000 μm.

3. The method of claim 1, wherein a tessellation ratio of openings of the at least two recesses in the bottom face of the well is from 5% to 99.9%.

4. The method of a cell cluster group according to claim 1, wherein a number of the at least two recesses in the well is from 2 to 500.

5. The method of claim 1, wherein a number of the dispersed cells in the cell suspension is from 10 cells/μL to 5,000 cells/μL.

6. The method of claim 1, wherein an extracellular matrix is mixed in the culture medium.

7. The method of claim 1, wherein an inner wall surface of each of the at least two recesses has cell-non-adhesiveness.

8. The method of claim 1, wherein an inner wall surface of each of the at least two recesses recess has a fine protrusion structure.

9. The method of claim 1, wherein the dispersed cells comprise dispersed gastrointestinal stem cells.

10. The method of claim 1, wherein the cell-cultivation container is centrifuged at a centrifugal force of from 200×g to 1000×g.

* * * * *